US010543478B2

(12) United States Patent
Cha et al.

(10) Patent No.: US 10,543,478 B2
(45) Date of Patent: Jan. 28, 2020

(54) CATALYST FOR OXIDATIVE DEHYDROGENATION AND METHOD OF PREPARING THE SAME

(71) Applicant: LG CHEM, LTD., Seoul (KR)

(72) Inventors: Kyong Yong Cha, Daejeon (KR); Myung Ji Suh, Daejeon (KR); Dong Hyun Ko, Daejeon (KR); Dae Heung Choi, Daejeon (KR); Ye Seul Hwang, Daejeon (KR); Jun Kyu Han, Daejeon (KR); Sun Hwan Hwang, Daejeon (KR); Seong Min Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 85 days.

(21) Appl. No.: 15/570,187

(22) PCT Filed: Mar. 7, 2017

(86) PCT No.: PCT/KR2017/002450
§ 371 (c)(1),
(2) Date: Oct. 27, 2017

(87) PCT Pub. No.: WO2017/164542
PCT Pub. Date: Sep. 28, 2017

(65) Prior Publication Data
US 2018/0133698 A1    May 17, 2018

(30) Foreign Application Priority Data

Mar. 24, 2016  (KR) .......................... 10-2016-0035268

(51) Int. Cl.
*B01J 21/10* (2006.01)
*B01J 23/00* (2006.01)
(Continued)

(52) U.S. Cl.
CPC ............. *B01J 23/745* (2013.01); *B01J 21/10* (2013.01); *B01J 23/02* (2013.01); *B01J 23/06* (2013.01);
(Continued)

(58) Field of Classification Search
CPC . B01J 21/10; B01J 23/00; B01J 23/005; B01J 23/02; B01J 23/06; B01J 23/10;
(Continued)

(56) References Cited

U.S. PATENT DOCUMENTS 8,674,156 B2 * 3/2014 Chung .................. B01J 23/002
502/324
9,550,174 B2 * 1/2017 Kwon .................. B01J 23/8892
(Continued)

FOREIGN PATENT DOCUMENTS

CN    103102238 A    5/2013
CN    103752316 A    4/2014
(Continued)

OTHER PUBLICATIONS

J.A. Toledo et al., "Oxidative dehydrogenation of 1-butene over Zn—Al ferrites", Journal of Molecular Catalysis A: Chemical, vol. 125, No. 1, Oct. 1, 1997 (Oct. 1, 1997), pp. 53-62, XP055069766.

*Primary Examiner* — Cam N. Nguyen
(74) *Attorney, Agent, or Firm* — Dentons US LLP

(57) ABSTRACT

The present invention relates to a method of preparing a catalyst for oxidative dehydrogenation. More particularly, the method of preparing a catalyst for oxidative dehydrogenation includes a first step of preparing an aqueous iron-metal precursor solution by dissolving a trivalent cation iron (Fe) precursor and a divalent cation metal (A) precursor in distilled water; a second step of obtaining a slurry of an iron-metal oxide by reacting the aqueous iron-metal precursor solution with ammonia water in a coprecipitation bath to
(Continued)

form an iron-metal oxide (step b) and then filtering the iron-metal oxide; and a third step of heating the iron-metal oxide slurry.

In accordance with the present invention, a metal oxide catalyst, as a catalyst for oxidative dehydrogenation, having a high spinel phase structure proportion may be economically prepared by a simple process.

8 Claims, 2 Drawing Sheets

(51) Int. Cl.
| | |
|---|---|
| B01J 23/02 | (2006.01) |
| B01J 23/06 | (2006.01) |
| B01J 23/10 | (2006.01) |
| B01J 23/34 | (2006.01) |
| B01J 23/72 | (2006.01) |
| B01J 23/745 | (2006.01) |
| B01J 23/78 | (2006.01) |
| B01J 23/80 | (2006.01) |
| B01J 23/889 | (2006.01) |
| B01J 37/00 | (2006.01) |
| C07C 1/22 | (2006.01) |
| C07C 1/24 | (2006.01) |

(52) U.S. Cl.
CPC ............... B01J 23/10 (2013.01); B01J 23/34 (2013.01); B01J 23/72 (2013.01); *C01P 2002/32* (2013.01); *C01P 2002/72* (2013.01); *C07C 1/22* (2013.01); *C07C 1/24* (2013.01)

(58) Field of Classification Search
CPC . B01J 23/34; B01J 23/72; B01J 23/745; B01J 23/78; B01J 23/80; B01J 23/8892; B01J 37/00
See application file for complete search history.

(56) References Cited

U.S. PATENT DOCUMENTS

| | | | |
|---|---|---|---|
| 10,315,969 B2 * | 6/2019 | Hwang | ................ B01J 35/0006 |
| 2012/0059208 A1 | 3/2012 | Mamedov et al. | |

FOREIGN PATENT DOCUMENTS

| | | |
|---|---|---|
| JP | 2015-0167886 A | 9/2015 |
| KR | 10-0847206 B1 | 7/2008 |
| KR | 10-2011-0036290 A | 4/2011 |
| KR | 101261124 B1 | 5/2013 |
| WO | 2009045002 A1 | 4/2009 |

* cited by examiner

[FIG. 1]
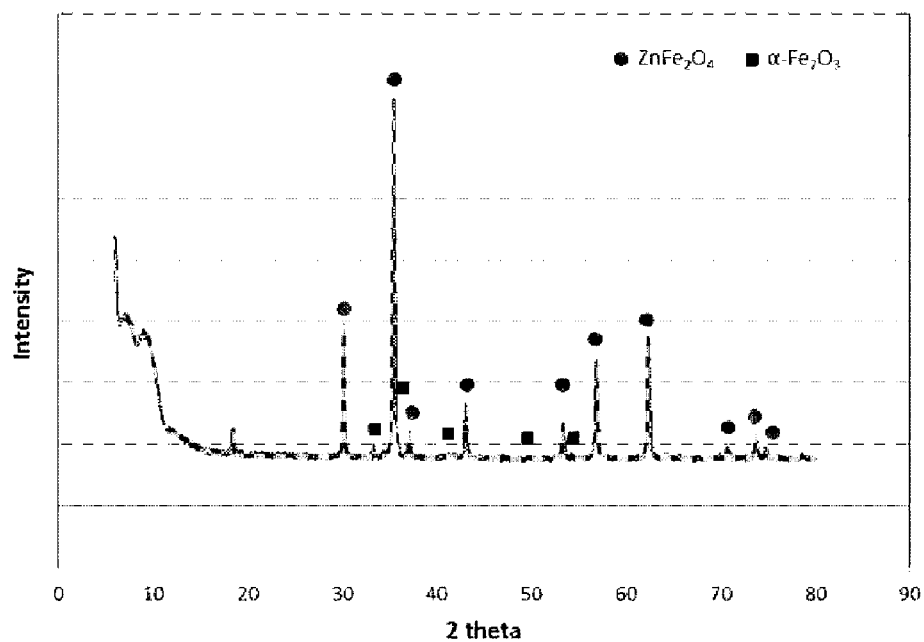
[FIG. 2]
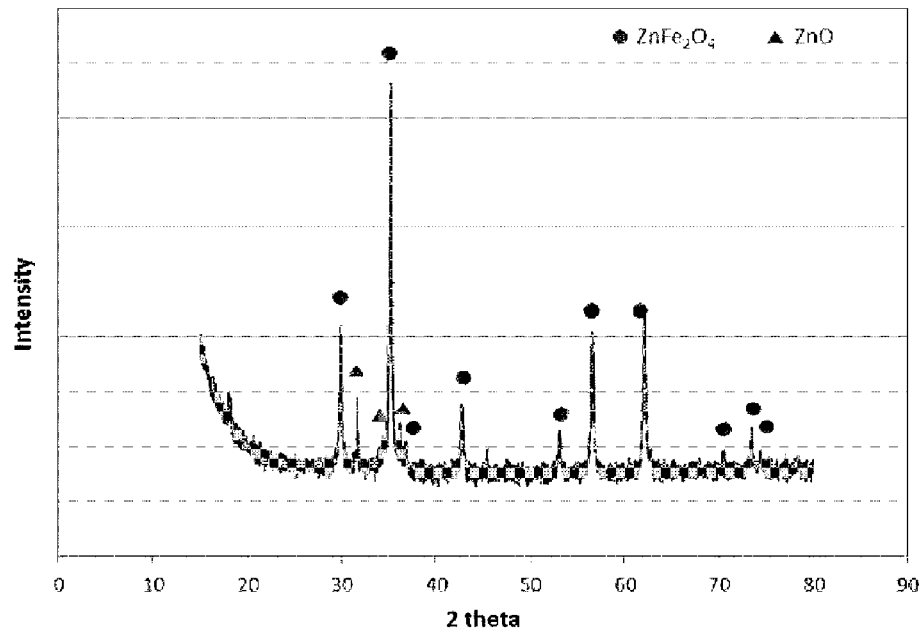

【FIG. 3】
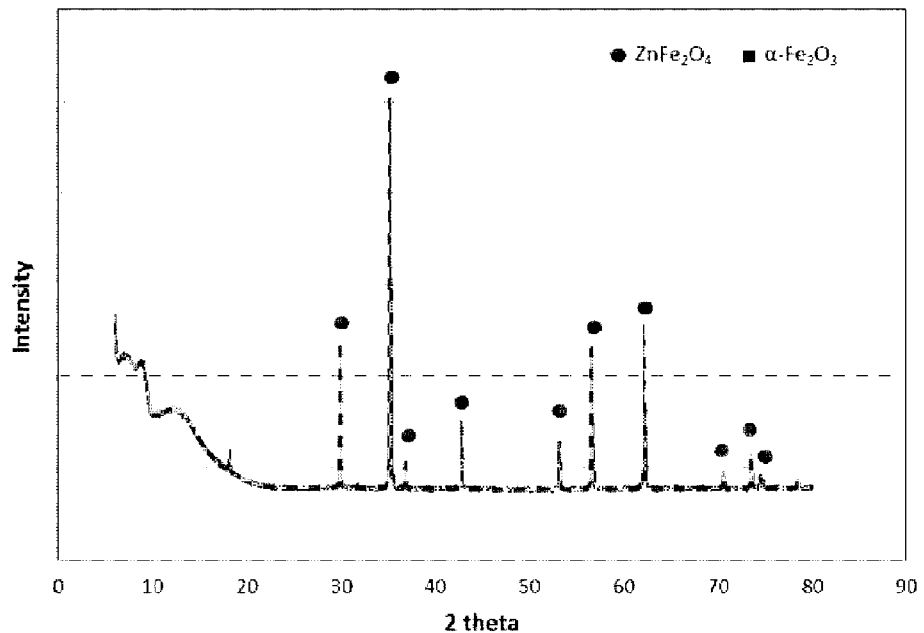
【FIG. 4】
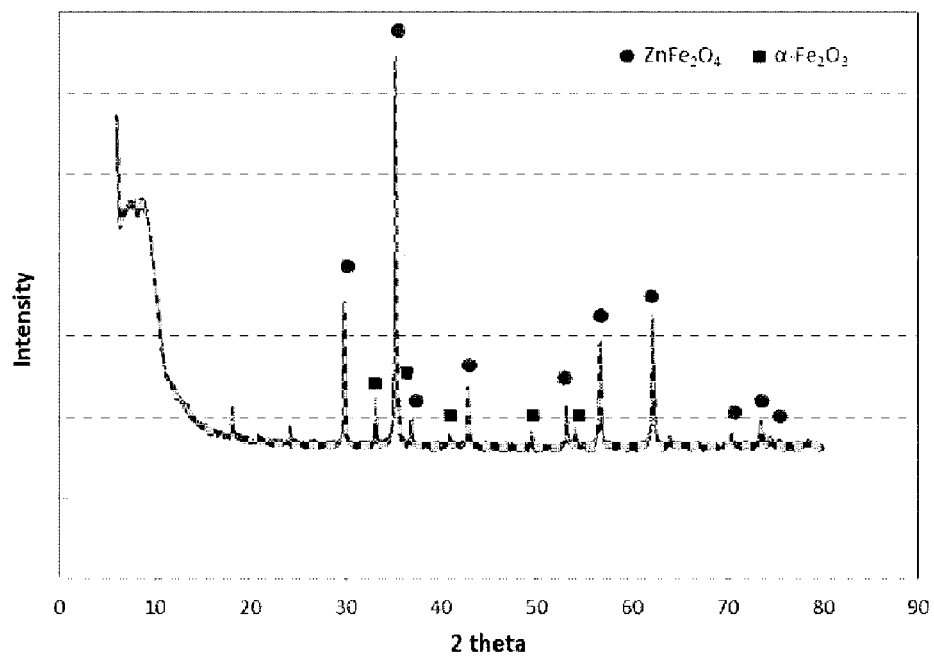

CATALYST FOR OXIDATIVE DEHYDROGENATION AND METHOD OF PREPARING THE SAME

CROSS-REFERENCE TO RELATED APPLICATION

This application is a National Stage Entry of International Application No. PCT/KR2017/002450, filed on Mar. 7, 2017, and claims the benefit of and priority to Korean Application No. 10-2016-0035268, filed on Mar. 24, 2016, all of which are hereby incorporated by reference in their entirety for all purposes as if fully set forth herein.

TECHNICAL FIELD

The present invention relates to a catalyst for oxidative dehydrogenation and a method of preparing the same. More particularly, the present invention relates to an economical catalyst for oxidative dehydrogenation, which provides superior butadiene generation efficiency and a preparation process of which is simple, and a method of simply, economically preparing the catalyst for oxidative dehydrogenation, i.e., a metal oxide catalyst.

BACKGROUND ART

Demand for 1,3-butadiene, which is an intermediate in petrochemical products, and the value thereof are gradually increasing throughout the world. To produce 1,3-butadiene, methods, such as naphtha cracking, direct butene dehydrogenation, and oxidative dehydrogenation of butene, have been used. However, in the case of naphtha cracking, energy consumption is high due to high reaction temperature. In addition, since naphtha cracking is not a process specifically designed for production of 1,3-butadiene, other basic oils, other than 1,3-butadiene, are disadvantageously produced as surplus products. Meanwhile, direct dehydrogenation of normal-butene is thermodynamically unfavorable. In addition, since direct dehydrogenation of normal-butene is an endothermic reaction, high-temperature and low-pressure conditions are required to produce 1,3-butadiene in a high yield. Accordingly, direct dehydrogenation of normal-butene is not suitable as a commercial process for producing 1,3-butadiene.

Meanwhile, since, in the case of oxidative dehydrogenation of butene wherein butene reacts with oxygen in the presence of a metal oxide catalyst to generate 1,3-butadiene and water, stable water is generated, oxidative dehydrogenation of butene is thermodynamically advantageous. In addition, since oxidative dehydrogenation of butene is an exothermic reaction unlike direct dehydrogenation of butene, oxidative dehydrogenation of butene may produce 1,3-butadiene in a high yield even at low reaction temperature, compared to direct dehydrogenation of butene. In addition, since oxidative dehydrogenation of butene does not require additional heat supply, oxidative dehydrogenation of butene may be considered an effective production process that produces only 1,3-butadiene and thus satisfies demand for 1,3-butadiene.

A metal oxide catalyst used in oxidative dehydrogenation may be synthesized by a precipitation method. Various synthetic parameters used in oxidative dehydrogenation are known to change a phase structure of a resultant precipitate, thereby affecting selectivity, yield, and the like of butadiene. Accordingly, although development of technologies related to various synthetic parameters has been continuously attempted, the selectivity and yield of butadiene are not sufficient yet. Therefore, continuous research into development of a ferrite catalyst capable of being simply and economically prepared and exhibiting superior performance is required.

RELATED ART DOCUMENT

Patent Document (Patent Document 1) JP 2015-167886 A

DISCLOSURE

Technical Problem

The present inventors observed that, while performing research into a method of preparing a metal oxide catalyst, the proportion of a spinel phase structure acting as oxidative dehydrogenation sites was limited because iron ions and metal ions remaining in a solution were discharged, in a considerable amount, with wastewater when an iron-metal oxide solution was filtered, generated wastewater was discharged by washing a filtrate, and a remaining filtrate was heated. Based on such an observation result, the present inventors completed the present invention.

That is, it is one object of the present invention to provide a method of preparing a catalyst for oxidative dehydrogenation capable of providing a high spinel phase structure proportion.

It is another object of the present invention to provide an economical catalyst for oxidative dehydrogenation, which provides superior butadiene generation efficiency and a preparation process of which is simple.

The above and other objects can be accomplished by the present disclosure described below.

Technical Solution

In accordance with one aspect of the present invention, provided is a method of preparing a catalyst for oxidative dehydrogenation, the method including a first step of preparing an aqueous iron-metal precursor solution by dissolving a trivalent cation iron (Fe) precursor and a divalent cation metal (A) precursor in distilled water; a second step of obtaining a slurry of an iron-metal oxide by reacting the aqueous iron-metal precursor solution with ammonia water in a coprecipitation bath to form an iron-metal oxide and then filtering the iron-metal oxide; and a third step of heating the iron-metal oxide slurry.

In accordance with another aspect of the present invention, provided is a catalyst for oxidative dehydrogenation, wherein the catalyst is an oxide catalyst including iron; and one or more divalent metals (A) selected from among Cu, Ra, Ba, St, Ca, Be, Zn, Mg, Mn, and Co, the catalyst including greater than 92% by weight and 99.9% by weight or less of a spinel phase ($AFe_2O_4$) and 0.1% by weight or more and less than 8% by weight of zinc oxide (ZnO).

Advantageous Effects

As apparent from the fore-going, the present invention advantageously provides a method of simply, economically preparing a metal oxide catalyst having a high spinel phase structure proportion, as a catalyst for oxidative dehydrogenation, and a catalyst for oxidative dehydrogenation providing high butadiene generation efficiency.

DESCRIPTION OF DRAWINGS

FIG. 1 illustrates X-ray diffraction (XRD) data of an iron-metal oxide catalyst (including a spinel phase and a zinc oxide) of the present invention. From this data, it can be confirmed that, when a filtrate is not subjected to a subsequent washing process, iron ions and metal ions remaining in a slurry of an iron-metal oxide are additionally bonded to a spinel phase structure, thereby providing a spinel phase content corresponding to a commercially available catalyst.

FIG. 2 illustrates XRD data of an iron-metal oxide catalyst (including a spinel phase and a zinc oxide) wherein iron ions and metal ions remaining in a filtrate are discharged with wastewater through a subsequent washing process of the filtrate according to a conventional technology. From this data, it can be confirmed that a spinel phase content is lower than in a commercially available catalyst.

FIG. 3 illustrates XRD data of a commercially available catalyst. From this data, it can be confirmed that a spinel phase content is 100% by weight.

FIG. 4 illustrates XRD data to investigate whether change in a synthesis condition affect a final catalyst ingredient, when iron ions and metal ions remaining in a slurry of an iron-metal oxide are additionally bonded to a spinel phase structure.

BEST MODE

Hereinafter, the present invention is described in detail.

A method of preparing a catalyst for oxidative dehydrogenation according to the present invention is described in detail.

The method of preparing a catalyst for oxidative dehydrogenation includes a first step of preparing an aqueous iron-metal precursor solution by dissolving a trivalent cation iron (Fe) precursor and a divalent cation metal (A) precursor in distilled water; a second step of obtaining a slurry of an iron-metal oxide by reacting the aqueous iron-metal precursor solution with ammonia water in a coprecipitation bath to form an iron-metal oxide and then filtering the iron-metal oxide; and a third step of heating the iron-metal oxide slurry.

In the first step, the trivalent cation iron (Fe) precursor and the divalent cation metal (A) precursor are dissolved in distilled water, thereby preparing the aqueous iron-metal precursor solution.

Each of the trivalent cation iron (Fe) precursor and the divalent cation metal (A) precursor is not specifically limited so long as they have been generally used in the art. For example, a metal salt including a trivalent cation iron (Fe) precursor and a divalent cation metal (A) ingredient may be used. As a particular example, a nitrate, ammonium salt, sulfate, or chloride of the metal ingredient may be used. Preferably, a chloride or a nitrate is used.

The divalent cation metal (A) may be, for example, one or more selected from the group consisting of divalent cation metals. As a particular example, the divalent cation metal (A) may be one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co). The divalent cation metal (A) may be preferably one or more selected from the group consisting of zinc (Zn), magnesium (Mg), manganese (Mn), and cobalt (Co), more preferably zinc (Zn) or manganese (Mn).

The trivalent cation iron (Fe) precursor and the divalent cation metal (A) precursor may be included, for example, in an atom number ratio of 1.5 to 10, 1.5 to 6, 1.5 to 5, or 1.5 to 2.5 (Fe/A, measured according to energy dispersive spectrometry (EDS)) in the aqueous iron-metal precursor solution. Within this range, a spinel-phase catalyst may be prepared without alpha-iron oxide in the catalyst, and, when applied to oxidative dehydrogenation of butadiene, process efficiency may be improved.

The aqueous iron-metal precursor solution may have, for example, a concentration of 1 to 15% by weight. Within this range, a spinel-phase catalyst may be prepared without alpha-iron oxide in the catalyst, and, when applied to oxidative dehydrogenation of butadiene, process efficiency may be improved.

In the second step, the aqueous iron-metal precursor solution and the ammonia water are reacted in a coprecipitation bath, thereby forming an iron-metal oxide solution.

The ammonia water may have, for example, a concentration of 20 to 40% by weight, 20 to 30% by weight, or about 25% by weight. Within this range, a spinel-phase catalyst may be prepared without alpha-iron oxide in the catalyst, and, when applied to oxidative dehydrogenation of butadiene, process efficiency may be improved. In addition, it is undesirable to use an aqueous metal basic solution instead of ammonia water because it may be difficult to prepare only a spinel-phase catalyst and wastewater may be generated.

A mole ratio of ions in the ammonia water to iron-metal cations in the aqueous iron-metal precursor solution, which are supplied in the second step, is preferably greater than 100:22 and less than 100:26, 100:23 to 100:25, 100:23 to 100:24, or 100:23.5 to 100:24.5. Within this range, a spinel-phase catalyst may be prepared without alpha-iron oxide in the catalyst.

For reference, when a mole ratio of the ions in the ammonia water to the iron-metal cations is 100:26 or more, the mole ratio is unsuitable for a synthesized catalyst. Accordingly, alpha-iron oxide capable of decreasing butadiene generation efficiency may be included in a large amount of 10% by weight or more. When a mole ratio of the ions in the ammonia water to the iron-metal cations is less than 100:22, the proportion of a spinel phase ingredient to be formed by coprecipitation is naturally limited. Accordingly, although iron ions and metal ions remaining in a solution are additionally precipitated, the content of a finally obtained spinel phase ingredient may be smaller than an ingredient content in a commercially available catalyst.

The ammonia water and aqueous iron-metal precursor solution supplied in the second step may be, for example, respectively discharged dropwise from separate outlets. In this case, it may be easy to control a supply amount of ammonia water.

The coprecipitation bath in the second step may be filled, for example, with water. In step b, a reaction temperature in the coprecipitation bath may be, for example, 20 to 30° C., 22 to 25° C., or room temperature.

A solution of the iron-metal oxide obtained in the second step may be further subjected to stirring; aging; and filtration. In this case, reaction in the iron-metal oxide solution may be sufficiently carried out.

The stirring, for example, is not specifically limited so long as it is a method generally performed in the art. For example, the stirring may be carried out using a stirrer for 30 minutes to 3 hours, 30 minutes to 2 hours, or 30 minutes to 1 hour 30 minutes.

The aging may be carried out, for example, for 30 minutes to 3 hours, 30 minutes to 2 hours, or 30 minutes to 1 hour 30 minutes.

The filtration is not specifically limited so long as it is a method generally used in the art. For example, the iron-metal oxide solution may be vacuumed and filtered. The filtration of the present invention is characterized by being a non-washing process (excluding a subsequent washing process). That is, the iron-metal oxide catalyst of the present invention is maintained in a slurry state (refers to all of wet iron-metal oxides without being subjected to a subsequent washing process after filtration and includes a wet cake) without being subjected to a subsequent washing process after discharge of a filtrate, thereby being precipitated in an additionally bonded shape by heating iron ions and metal ions remaining in the slurry as described below.

In the third step, the iron-metal oxide slurry is heated, thereby forming an iron-metal oxide catalyst in which iron ions and metal cations present in the slurry are precipitated in a bonded shape.

In the third step, the heating of the iron-metal oxide slurry may be carried out in two steps, i.e., a drying step and a firing step.

The drying step may be carried out, for example, at 60 to 100° C., 70 to 100° C., or 80 to 100° C. for 12 to 20 hours, 14 to 20 hours, or 14 to 18 hours by means of a general dryer.

The firing step may be carried out, for example, at 400 to 800° C., 500 to 800° C., or 550 to 750° C. for 1 to 10 hours, 3 to 8 hours, or 5 to 7 hours using a general furnace. A method of firing is not specifically limited so long as it is a heat treatment method generally used in the art.

As a result, in the iron-metal oxide catalyst formed in the third step of the present disclosure, a ratio of an iron (Fe) atom number to a metal (A) atom number is 1.5:1 to 4:1, or 1.5:1 to 2.5:1. Accordingly, the present invention has an advantage in maintaining an atom number ratio of the trivalent cation iron (Fe) to the divalent cation metal (A), which are supplied in the first step, by a simple process.

Such an advantage is provided by controlling a supply ratio of ammonia water to an iron-metal precursor such that an optimal reaction of forming a spinel phase structure is carried out, and maintaining a slurry state without a subsequent washing process after filtering an iron-metal oxide catalyst, as a reaction product, and removing a resultant filtrate such that unreacted iron ions and metal cations remaining in the slurry are not discharged by washing and are maximally used to prepare a catalyst.

In accordance with the aforementioned method, a catalyst having a spinel phase structure may be prepared in a chemically stable manner without removal of iron ions and metal cations, which have been removed by washing, remaining in a slurry. For example, a catalyst obtained according to the aforementioned method is, for example, an oxide catalyst including iron; and one or more divalent metals (A) selected from among Cu, Ra, Ba, St, Ca, Be, Zn, Mg, Mn, and Co, and may provide a spinel phase ingredient content corresponding to a commercially available catalyst.

An atom number ratio of the iron (Fe) to the divalent metal (A) in the catalyst may be 1.5:1 to 4:1, preferably 1.5:1 to 2.5:1, as described above.

The catalyst for oxidative dehydrogenation of the present disclosure is an oxide catalyst including iron; and one or more divalent metals (A) selected from among Cu, Ra, Ba, St, Ca, Be, Zn, Mg, Mn, and Co. For example, the catalyst for oxidative dehydrogenation of the present disclosure may include greater than 92% by weight and 99.9% by weight or less of a spinel phase ($AFe_2O_4$) and 0.1% by weight or more and less than 8% by weight of zinc oxide (ZnO), or 96 to 99.9% by weight of a spinel phase and 0.1 to 4% by weight of zinc oxide (ZnO). Within these ranges, iron ions and zinc ions, which have been discarded through wastewater, remaining in a solution, are additionally used, thereby preparing a catalyst preparing having a spinel phase structure. Accordingly, catalyst preparation efficiency may be remarkably improved.

When the catalyst of the present disclosure, as a catalyst for oxidative dehydrogenation, is used to produce butadiene from a raffinate by oxidative dehydrogenation, improved process efficiency may be provided due to a spinel phase ingredient content corresponding to a commercially available catalyst.

A method of preparing the butadiene is not specifically limited so long as it is a method generally used in the art, and those skilled in the art may variously modify the method applying the following experimental examples.

Now, the present invention will be described in more detail with reference to the following preferred examples. However, these examples are provided for illustrative purposes only. Those skilled in the art will appreciate that various modifications, additions and substitutions are possible, without departing from the scope and spirit of the invention. Therefore, it is obvious that the modifications, additions and substitutions are within the scope of the present invention.

EXAMPLE

Example 1

In a first step, 12.0 g of zinc nitrate ($ZnNO_3$) and 47.7 g of ferric chloride ($FeCl_3$) were dissolved in 835.5 ml of distilled water, thereby preparing 895.2 g of an aqueous iron-metal precursor solution. Here, an atom number ratio of the metal ingredients, i.e., Fe to Zn, included in the aqueous iron-metal precursor solution was as follows: Fe:Zn=2:1.

In a second step, a coprecipitation bath filled with 8500 ml of water was equipped with an outlet for the aqueous iron-metal precursor solution and an outlet for ammonia water. While adding the aqueous iron-metal precursor solution dropwise through the aqueous iron-metal precursor solution outlet, ammonia water at a concentration of 25% was added dropwise through the ammonia water outlet over a period of 20 minutes such that a mole ratio of ions in the ammonia water to iron-zinc cations in the aqueous iron-metal precursor solution was maintained at 100:24.

After completing the addition of the aqueous iron-metal precursor solution, an obtained iron-metal oxide solution was stirred using a stirrer for one hour such that reaction (coprecipitation) was sufficiently performed.

After stopping the stirring, the iron-metal oxide solution was allowed to sit at room temperature for one hour such that a precipitate completely sank, thereby being phase-separated. Subsequently, a coprecipitation solution was vacuum-filtered by means of a vacuum filter to discharge a filtrate. A residual filtrate was not subjected to a subsequent washing process. As a result, a slurry of an iron-metal oxide was obtained.

In a third step, the iron-metal oxide slurry was dried at 90° C. for 16 hours, and then a dried precipitate was put into a furnace and heat-treated at 650° C. for 6 hours. As a result, a zinc ferrite catalyst was prepared.

FIG. 1 illustrates an X-ray diffraction (XRD) graph of the prepared zinc ferrite catalyst. Referring to FIG. 1, it can be confirmed that the catalyst consists of 98% by weight of a spinel phase and 2% by weight of zinc oxide due to additional bonding of iron ions and metal ions remaining in the iron-metal oxide solution to a spinel phase structure. The content of the spinel phase corresponds to that in a commercially available catalyst.

Comparative Example 1

In the second step of Example 1, an iron-metal oxide solution was stirred and aged, and then vacuum-filtered using a filter to discharge a filtrate. Subsequently, 5 L of wastewater was discharged through a washing process, and a residual filtrate was vacuum-separated using filter paper. Subsequently, the third step of Example 1 was performed, thereby preparing a zinc ferrite catalyst.

FIG. 2 illustrates an X-ray diffraction (XRD) graph of the prepared zinc ferrite catalyst. Referring to FIG. 2, it can be confirmed that the catalyst consists of a spinel phase content of 78% by weight and a zinc oxide of 22% by weight, which are smaller than in a commercially available catalyst, because iron ions and metal ions remaining in a filtrate are discharged with wastewater by subjecting the filtrate to a subsequent washing process according to a conventional technology.

Test Example

Comparison of Atom Number Ratios of Fe to Zn in Catalysts:

Elements were analyzed using dispersive spectrometry (EDS). For example, atom numbers in the catalyst of each of Example 1 and Comparative Example 1 were measured. Results are summarized in Table 1 below.

TABLE 1

| EDS results (Atomic %) | Example 1 (washing not performed—O L of wastewater discharged) | Comparative Example 1 (washing performed—5 L of wastewater discharged) |
| --- | --- | --- |
| Oxygen atoms | 60.1 | 66.29 |
| Chlorine atoms | 0.1 | 0.04 |
| Iron atoms | 27.8 | 18.91 |
| Zinc atoms | 11.9 | 14.76 |
| Fe/Zn (atom number ratio) | 2.3 | 1.3 |

As shown in Table 1, an atom number ratio of iron to zinc in Example 1 according to the present disclosure is 2.3 which is not greatly different from the ratio of iron to zinc (2:1) added in the first step of Example 1. As a result, it can be confirmed that losses of the iron ions and the zinc ions are not large.

On the other hand, in the case of Comparative Example 1, an atom number ratio of iron to zinc is 1.3, which indicates that loss of the iron ions and the zinc ions is large. Such a result can be interpreted as occurring because iron ions having a relatively small particle size are lost more in a washing process and some of zinc ions forming an outside of a catalyst lattice are lost with iron ions.

EXPERIMENTAL EXAMPLE

Experimental Example 1

An experiment was carried out in the same manner as in Example 1, except that, in the first step, ions of the ammonia water and iron-zinc cations in the aqueous iron-metal precursor solution were added in a mole ratio of 100:25.

As an X-ray diffraction (XRD) result of a prepared zinc ferrite catalyst, it was confirmed that the zinc ferrite catalyst was composed of 96.7% by weight of a spinel phase and 3.3% by weight of zinc oxide.

Experimental Example 2

An experiment was carried out in the same manner as in Example 1, except that, in the first step, ions of the ammonia water and iron-zinc cations in the aqueous iron-metal precursor solution were added in a mole ratio of 100:23.

As an X-ray diffraction (XRD) result of a prepared zinc ferrite catalyst, it was confirmed that the zinc ferrite catalyst was composed of 96.7% by weight of a spinel phase and 3.3% by weight of zinc oxide.

ADDITIONAL EXPERIMENTAL EXAMPLES

Additional Experimental Example 1

A zinc ferrite catalyst having 100% by weight of a spinel phase structure (ZnFe2O4) manufactured by Kojundo Chemical Laboratory and commercially available was prepared.

The commercially available catalyst was heat-treated as in the third step of Example 1 and then subjected to XRD. A result is shown in FIG. 3. As illustrated in FIG. 3, the catalyst was confirmed as having 100% by weight of a spinel phase structure.

Additional Experimental Example 2

An experiment was carried out in the same manner as in Example 1, except that, in the second step, ammonia water at a concentration of 25% was added dropwise to a coprecipitation bath filled with 8500 ml of water through an outlet for an aqueous iron-metal precursor solution over a period of 20 minutes through an outlet for ammonia water while adding the aqueous iron-metal precursor solution dropwise thereto such that a mole ratio of ions in the ammonia water to iron-zinc cations in the aqueous iron-metal precursor solution was maintained at 100:22. As a result, a catalyst was prepared.

An obtained catalyst was subjected to XRD. A result is shown in FIG. 4. As illustrated in FIG. 4, it can be confirmed that the catalyst is composed of 85% by weight of a spinel phase and 15% by weight of alpha-iron oxide ($\alpha$-$Fe_2O_3$)a when iron ions and metal ions remaining in an iron-metal oxide solution are additionally bonded to a spinel phase structure and a mole ratio, as a synthesis condition, is changed to a ratio of 100:22.

Additional Experimental Example 3

An experiment was carried out in the same manner as in Example 1, except that, in the first step, a mole ratio of ions in the ammonia water to iron-zinc cations in the aqueous iron-metal precursor solution was 100:26.

As an X-ray diffraction (XRD) result of the prepared zinc ferrite catalyst, it was confirmed that the catalyst was composed of 91.6% by weight of a spinel phase and 8.4% by weight of zinc oxide.

[Butadiene Preparation Test]

Using the catalyst for oxidative dehydrogenation prepared according to each of Example 1, Comparative Example 1, and Additional Experimental Examples 1 to 3, butadiene was prepared according to the following method.

Results are summarized in Table 2 below.

In particular, a mixture of 1-butene, trans-2-butene, and cis-2-butene and oxygen were used as reactants, and nitrogen and steam were additionally introduced along with the reactants. Here, a metallic tubular reactor was used. An atom number ratio of oxygen to butene (OBR), an atom number ratio of steam to butene (SBR), and an atom number ratio of nitrogen to butene (SBR), as ratios between reactants, and gas hourly space velocity (GHSV) were set as summarized in Table 2 below.

A fixed-bed reactor was filled with each of the obtained catalysts, and the volume of a catalyst layer contacting the reactants was fixed to 10 cc. Steam was introduced thereinto. Here, the steam was vaporized at 150° C. by means of a vaporizer and mixed with the reactants, i.e., the butene mixture and the oxygen, such that the steam was flowed along with the reactants into the reactor. The amount of the butene mixture was adjusted by means of a mass flow controller for liquids, the amounts of oxygen and nitrogen were adjusted by means of a mass flow controller for gases, and the amount of steam was adjusted by an injection rate thereof by means of a liquid pump.

Reaction temperatures were maintained as summarized in Table 2 below. Products after reaction were analyzed by gas chromatography (GC). Conversion rates of butene mixtures, conversion rates of butene in mixtures (corresponding to a conversion rate of a total of three kinds of X-> 1-butene, trans-2-butene, and cis-3-butene), 1,3-butadiene selectivity (S), and 1,3-butadiene yields (Y) were calculated according to Equations 1 to 3 below based on results measured by gas chromatography:

Conversion rate (%)=(Number of moles of reacted butene/number of moles of supplied butene)×100  [Equation 1]

Selectivity (%)=(Number of moles of generated 1,3 butadiene or $CO_X$/number of moles of reacted butene)×100  [Equation 2]

Yield (%)=(Number of moles of generated 1,3 butadiene/number of moles of supplied butene)×100  [Equation 3]

In addition, it can be confirmed that, in the case of Additional Experimental Example 1 wherein butadiene is prepared by subjecting a commercially available catalyst to oxidative dehydrogenation, a butene conversion rate, butadiene selectivity, and a yield are poor although a spinel phase ingredient content similar to the catalyst of Example 1 is provided.

Further, it can be confirmed that, in the cases of Additional Experimental Examples 2 and 3 carried out in the same manner as in Example 1 except for a mole ratio of ions of ammonia water to cations of an iron-zinc cations precursor (particularly, the mole ratios in Additional Experimental Examples 2 and 3 are respectively 100:22 and 100:26), a butene conversion rate, butadiene selectivity, and a yield are poor compared to Example 1.

The invention claimed is:

1. A method of preparing a catalyst for oxidative dehydrogenation, the method comprising:
   a first step of preparing an aqueous iron-metal precursor solution by dissolving a trivalent cation iron (Fe) precursor and a divalent cation metal (A) precursor in distilled water;
   a second step of obtaining a slurry of an iron-metal oxide by reacting the aqueous iron-metal precursor solution with ammonia water in a coprecipitation bath to form an iron-metal oxide and then filtering the iron-metal oxide; and
   a third step of heating the iron-metal oxide slurry,
   wherein a mole ratio of ions of the ammonia water supplied in the second step to iron-metal cations in the aqueous iron-metal precursor solution is greater than 100:22 and less than 100:26.

TABLE 2

| Classification | Conditions | | | | | X (Equation 1) | S-BD (Equation 2) | Y (Equation 3) |
| --- | --- | --- | --- | --- | --- | --- | --- | --- |
| | GHSV (h-1) | Temp (° C.) | OBR | SBR | NBR | | | |
| Example 1 | 500 | 340 | 0.75 | 15 | 3 | 86.9 | 90.6 | 78.7 |
| Comparative Example 1 | 500 | 340 | 0.75 | 15 | 3 | 80.9 | 87.9 | 71.1 |
| Additional Experimental Example 1 | 500 | 340 | 0.75 | 15 | 3 | 48.4 | 88.4 | 42.7 |
| Additional Experimental Example 2 | 500 | 360 | 0.75 | 15 | 3 | 75.5 | 87.8 | 66.3 |
| Additional Experimental Example 3 | 500 | 360 | 0.75 | 15 | 3 | 77.1 | 86.9 | 67.0 |

As shown in Table 2, it can be confirmed that, when butadiene is prepared by subjecting the catalyst of Example 1, which is prepared by additionally binding iron ions and metal ions remaining in a slurry according to the present invention, to oxidative dehydrogenation, all of a butene conversion rate, butadiene selectivity, and a yield are superior.

On the other hand, it can be confirmed that, when butadiene is prepared by subjecting the catalyst of Comparative Example 1, wherein iron ions and metal ions remaining in a filtrate are discharged in a considerable amount by discharging wastewater generated by subjecting a filtrate to a subsequent washing process according to a conventional technology, to oxidative dehydrogenation, all of a butene conversion rate, butadiene selectivity, and a yield are poor.

2. The method according to claim 1, wherein, before the filtering of the iron-metal oxide obtained in the second step, stirring and aging steps are further performed.

3. The method according to claim 2, wherein, when the filtering is performed, washing is not performed.

4. The method according to claim 1, wherein the heating of the iron-metal oxide slurry in the third step comprises drying and firing.

5. The method according to claim 1, wherein a ratio of an iron (Fe) atom number to a metal (A) atom number in an iron-metal oxide catalyst formed in the third step is 1.5:1 to 4:1.

6. The method according to claim 1, wherein the trivalent cation metal (A) is one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co).

7. The method according to claim 1, wherein the aqueous iron-metal precursor solution of the first step is prepared by dissolving a trivalent cation iron (Fe) precursor and a divalent cation metal (A) precursor, in an atom number ratio of 1.5:1 to 2.5:1, in distilled water.

8. The method according to claim 1, wherein the coprecipitation bath is equipped with a first outlet for the aqueous iron-metal precursor solution and a second outlet for the ammonia water, and in the second step, the aqueous iron-metal precursor solution is discharged dropwise from the first outlet and the ammonia water is discharged dropwise from the second outlet.

* * * * *